United States Patent
Meyer et al.

(10) Patent No.: US 8,292,900 B2
(45) Date of Patent: Oct. 23, 2012

(54) SIDE BRANCH WIRING ASSIST SHEATH AND METHODS

(75) Inventors: Michael Meyer, Maple Grove, MN (US); Michael Wayne Davis, Rockford, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 947 days.

(21) Appl. No.: 12/136,290

(22) Filed: Jun. 10, 2008

(65) Prior Publication Data

US 2009/0306757 A1   Dec. 10, 2009

(51) Int. Cl.
*A61F 11/00* (2006.01)
*A61M 25/00* (2006.01)
(52) U.S. Cl. .................. 606/108; 600/585; 604/284
(58) Field of Classification Search .............. 623/1.11, 623/1.12, 1.23; 606/108; 600/433–435, 600/585; 604/284
See application file for complete search history.

(56) References Cited

U.S. PATENT DOCUMENTS

| | | | |
|---|---|---|---|
| 6,146,356 A | | 11/2000 | Wang et al. |
| 6,217,527 B1 * | | 4/2001 | Selmon et al. ............. 600/585 |
| 6,682,536 B2 * | | 1/2004 | Vardi et al. ................ 606/108 |
| 7,172,551 B2 * | | 2/2007 | Leasure ...................... 600/16 |
| 2004/0073108 A1 * | | 4/2004 | Saeed et al. ................ 600/431 |
| 2006/0293695 A1 * | | 12/2006 | Ricci et al. ................. 606/108 |
| 2007/0250001 A1 | | 10/2007 | Hilaire et al. |
| 2008/0109061 A1 * | | 5/2008 | Gregorich et al. ......... 623/1.12 |
| 2008/0228165 A1 * | | 9/2008 | Spence et al. .............. 604/510 |
| 2009/0204083 A1 * | | 8/2009 | O'Donnell et al. ........ 604/284 |

FOREIGN PATENT DOCUMENTS

WO   0145785   6/2001
WO   2009102591   8/2009

* cited by examiner

*Primary Examiner* — Katherine Dowe
(74) *Attorney, Agent, or Firm* — Seager, Tufte & Wickhem, LLC

(57) ABSTRACT

A vessel bifurcation wire assist device and related methods of advancing guidewires into main and branch vessels of a vessel bifurcation. The wire assist device includes a first guidewire housing member defining a first guidewire lumen sized to advance over a first guidewire, and a second guidewire housing member defining a second guidewire lumen sized to advance over a second guidewire. The second guidewire housing member has a first directional arrangement and a second directional arrangement. The first directional arrangement provides a parallel arrangement of the second guidewire relative to the first guidewire housing member, and the second directional arrangement provides an angled arrangement of the second guidewire relative to the first guidewire housing member.

4 Claims, 5 Drawing Sheets

SIDE BRANCH WIRING ASSIST SHEATH AND METHODS

TECHNICAL FIELD

This disclosure relates to devices and methods for treatment of a vessel bifurcation.

BACKGROUND

Catheters are used with stents and inflatable structures to treat conditions such as strictures, stenoses, and narrowing in various parts of the body. Various catheter designs have been developed for the dilatation of stenoses and to deliver and deploy stents at treatment sites within the body.

Stents are typically intraluminally placed by a catheter within a vein, artery, or other tubular shaped body organ for treating conditions such as, for example, occlusions, stenoses, aneurysms, dissections, or weakened, diseased, or abnormally dilated vessels or vessel walls, by expanding the vessels or by reinforcing the vessel walls. Once delivered, the stents can be expanded using one or more inflatable members such as balloons. Stents can improve angioplasty results by preventing elastic recoil and remodeling of the vessel wall and treating dissections in blood vessel walls caused by balloon angioplasty of coronary arteries. Stents can also be used as a drug delivery medium for treatment of damaged portions of a vessel.

While conventional stent technology is relatively well developed, stent technologies related to treatment of the region of a vessel bifurcation are still being developed. One challenge related to treatment of a vessel bifurcation involves advancing guidewires into position in the vessels of a vessel bifurcation.

SUMMARY OF THE DISCLOSURE

The present disclosure relates to a vessel bifurcation wire assist device and related methods of advancing guidewires into main and branch vessels of a vessel bifurcation. According to one aspect of the present disclosure, a wire assist device includes a first guidewire housing member defining a first guidewire lumen sized to advance over a first guidewire. The wire assist device also includes a second guidewire housing member defining a second guidewire lumen sized to advance over a second guidewire and being axially fixed relative to the first guidewire housing member. The second guidewire housing member has a first directional arrangement and a second directional arrangement. The first directional arrangement provides a parallel arrangement of the second guidewire relative to the first guidewire housing member, and the second directional arrangement provides an angled arrangement of the second guidewire relative to the first guidewire housing member.

The wire assist device is configured to advance over the main and branch guidewires within a main vessel of the vessel bifurcation to a position adjacent to an opening into the branch vessel. The second guidewire housing member in the second directional arrangement is configured to direct the branch guidewire from a position within the main vessel to a position extending into the branch vessel as the branch guidewire is advanced distally through the second guidewire housing.

There is no requirement that an arrangement includes all features characterized herein to obtain some advantage according to this disclosure.

DETAILED DESCRIPTION

This disclosure relates to bifurcation treatment systems, catheter assemblies, and related methods of treating bifurcations in a patient's body. The term bifurcation means a division location from one unit into two or more units. Generally, two types of bifurcations of a body organ include: 1) a main tubular member defining a main lumen and a branch tubular member defining a branch lumen that extends or branches off from the main tubular member, wherein the main and branch lumens are in fluid communication with each other, and 2) a primary or main member defining a primary or main lumen (also referred to as a parent lumen) that splits into first and second branch members defining first and second branch lumens. The term lumen means the cavity or bore of a tubular structure such as a tubular organ (e.g., a blood vessel).

An example bifurcation is a vessel bifurcation that includes a continuous main vessel and a branch vessel, wherein the vessels define a main lumen and a branch lumen, respectively that are in fluid communication with each other. Alternatively, a vessel bifurcation can include a parent vessel that divides into first and second branch vessels, wherein the vessels define a parent lumen and first and second branch lumens, respectively, which lumens are all in fluid communication with each other.

Example applications of the inventive principles disclosed herein include cardiac, coronary, renal, peripheral vascular, gastrointestinal, pulmonary, urinary, and neurovascular systems. The systems and methods disclosed herein can be used for locating a branch vessel of the vessel bifurcation and for placement of a guidewire within the branch vessel. With a main guidewire positioned in a main vessel of the vessel bifurcation and the branch guidewire positioned in the branch vessel of the vessel bifurcation, a catheter assembly can be advanced over the main and branch guidewires into a treatment position adjacent the vessel bifurcation. Some catheter assembly arrangements can include self-alignment capabilities to align features of the catheter assembly (e.g., a side opening of the stent of the catheter assembly) with the opening into the branch vessel when the catheter assembly can be advanced over a branch guidewire that is pre-positioned in the branch vessel.

Directing a branch guidewire into a branch vessel of a vessel bifurcation can be challenging for several reasons. Typically, a branch vessel has a smaller diameter than the main vessel from which the branch vessel extends, which can result in a relatively small access opening (i.e. ostium) into the branch vessel. The small size of the opening into the branch vessel can be further reduced when plaque or other damage to the vessel bifurcation exists in the area of the opening into the branch vessel. Branch vessels also extend off from the main vessel at an angle, typically in the range of about 30° to about 90°. A branch guidewire positioned in the main vessel is usually arranged along the longitudinal axis of the main vessel, making it difficult to direct the tip of the branch guidewire at the angle of the branch vessel.

Some types of guidewires used for the branch guidewire include a pre-formed bend at the distal tip thereof. Such a pre-bent tip can help in directing the branch guidewire in an angled direction, but not always at the same angle as the angle of the branch vessel. A further complication with directing the branch guidewire into the branch vessel is present when the branch vessel extends from the main vessel at a bend section of the main vessel. Maintaining a pre-bent tip of a branch guidewire at a desired rotated position along a bend portion of the main vessel can be especially difficult as the bent tip of the branch vessel tends to rotate to a rest state where the least torque is present, which may not be at the rotated angle where the branch vessel extends from the main vessel.

A still further challenge with directing a branch guidewire into a branch vessel relates to relative twist between the main guidewire and the branch guidewire along the lengths of the guidewire. The main guidewire is typically first advanced to the vessel bifurcation until a distal end thereof extends distal of the opening into the branch vessel. A guidewire is usually maintained in the main vessel until after the vessel bifurcation is treated (e.g., using angioplasty or stent placement at the vessel bifurcation). The branch guidewire tends to wrap around the main guidewire as the branch guidewire is navigated to the vessel bifurcation, causing relative twist between the guidewires. This relative twist can cause difficulties for the catheter assembly to later be advanced over the guidewires to the vessel bifurcation. Furthermore, this relative twist can make it more difficult to make axial and radial adjustments to the branch guidewire when attempting to direct the branch guidewire into the branch vessel.

The Example Wire Assist Devices of FIGS. 1-8

The example wire assist device is described below with reference to FIGS. 1-8 to provide systems and methods for advancing a branch guidewire into a branch vessel of a vessel bifurcation. The systems and methods can also be used to reduce relative twist between a main guidewire and a branch guidewire that are positioned at a vessel bifurcation.

Figure 1:
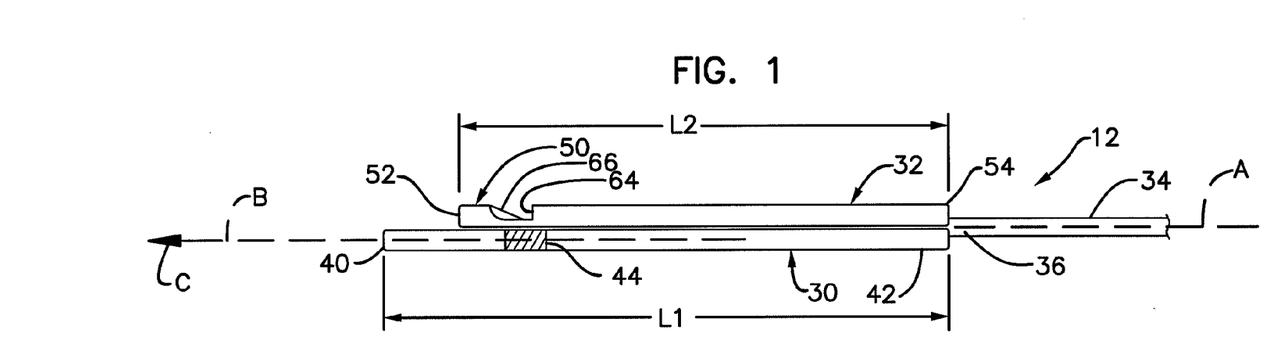
FIG. 1 is a schematic side view of an example wire assist device in accordance with principles of the present disclosure, wherein the wire assist device includes a side opening.

FIG. 1 illustrates a wire assist device 12 that includes a first guidewire housing member 30 and a second guidewire housing member 32. The first guidewire housing member 30 includes an open distal end 40, an open proximal end 42, and a marker member 44. The first guidewire housing member 30 defines a main guidewire lumen (not shown) sized to receive a main guidewire for advancement of the first guidewire housing member over the main guidewire. The housing members 30, 32 are typically coupled or otherwise connected together at some point along the length of one of the housing members 30, 32, or otherwise secured to a common member such as the shaft 34 described below such that the housing members 30 and 32 are axially fixed relative to each other. Structures that are axially fixed relative to each other are not moveable in an axial direction (i.e. along the length direction) relative to each other. Although alternatives are possible, some example ways of securing the housing members 30, 32 together include adhesives, heat welding, and laser welding. In some arrangements, at least portions of the housing members are co-extruded as an integral piece.

The second guidewire housing member 32 includes a distal end portion 50, an open distal end 52, an open proximal end 54, and a bend region 56. A second guidewire housing member 32 defines a branch guidewire housing sized to receive a branch guidewire to provide advancement of the second guidewire housing member 32 over the branch guidewire.

The distal end portion 50 includes a side opening 64 and a flap 66. The flap 66 can define a ramp surface. The ramp surface defined by flap 66 can help direct a distal tip of a branch guidewire in an angled direction (i.e. an angle greater than 0° and less than 180°) relative to, for example, a longitudinal axis A of the wire assist device 12, a longitudinal axis B of the first guidewire housing 30, or a length direction C of the first guidewire housing 30 (see FIG. 1). Arranging one structure (e.g., the branch guidewire) at a non-parallel orientation relative to another structure (e.g., the first guidewire housing member 30) can be defined as an "angled arrangement."

Positioning the branch guidewire in engagement with the ramp surface defined by flap 66 can be referred to as particular directional arrangement of the second guidewire housing member 32 in which the branch guidewire is arranged at an angle relative to another feature of the wire assist device 10. Positioning the branch guidewire in the second guidewire housing member 32 and not in engagement with the flap 66 or protruding through the side opening 64 can be referred to as a different directional arrangement of the second guidewire housing member 32 in which the branch guidewire is arranged in parallel with another feature of the wire assist device 10 (e.g., in parallel with longitudinal axis A, longitudinal axis B, or a length direction C).

The side opening 64 can be defined by cutting a portion of a side wall of the second guidewire housing member 32 while maintaining a connection point of the flap 66 at a distal end thereof to the second guidewire housing member 32. In other arrangements, the side opening 64 can include a complete removal of material in the side wall of the second guidewire housing member 32, or otherwise formation of the second guidewire housing member 32 with the side opening 64 defined in the sidewall thereof. The flap can be provided as a separate member that is secured to the second guidewire housing member 32 adjacent to the side opening 64 so that at least a portion of the flap extends into the second guidewire housing member 32.

Attachment of the flap 66 at a distal end of the side opening 64 permits advancement of a proximal end of the branch guidewire 16 into the open distal end 52 of the second guidewire housing member 32 and proximally past the flap 66 within the second guidewire housing member 32. The second guidewire housing member 32 can be advanced over the branch guidewire 16 to the distal end of the branch guidewire 16. Once the second guidewire housing member 32 is advanced distally to a point where the distal end of the branch guidewire 16 is positioned proximal of the side opening 64 and flap 66, the flap 66 can rest down within the branch guidewire lumen of the second guidewire housing member 32 to obstruct distal advancement of the branch guidewire 16 within the second guidewire housing member 32. The flap 66 can define a ramp surface that the distal tip of the branch guidewire 16 engages when advanced distally.

With the distal tip of the branch guidewire 16 positioned proximal of the side opening 64, advancing the branch guidewire distally engages the distal end of the branch guidewire with the ramp surface defined by flap 66 to direct the distal end of the branch guidewire in an angled direction relative to, for example, the longitudinal axis B of the first guidewire housing member 30. A further description of operation of the second guidewire housing member 32 of the wire assist device 12 relative to a branch guidewire 16 is described below with reference to FIGS. 9-13.

The marker member 44 positioned on the first guidewire housing member 30 can be positioned in axially alignment with a feature of the second guidewire housing member 32. The terms "axial alignment" and "axially aligned" are defined as alignment of features in an axial direction. For example, a feature positioned at a location along a length of a first structure is in axial alignment with a feature positioned at a location along a length of a second structure if the features are at the same distal or proximal location regardless of how far apart in the radial or lateral direction the features are relative to each other.

While alternatives are possible, the marker member 44 can be axially aligned with the side opening 64 and the flap 66. The marker member 44 can provide visualization for the operator under, for example, fluoroscopy or other visualization techniques that permit viewing of the wiring assist device 10 within a patient. In operation, the marker member 44 can be aligned with an opening into a branch vessel of the vessel bifurcation. In other arrangements, more than one marker member 44 can be used with the wire assist device 12. For example, marker members can be positioned along each of the housing members 30, 32 such as at the distal ends thereof. Alternatively, at least one marker member can be positioned at an axial position that indicates the location at which the branch guidewire is directed at an angle relative to the first guidewire housing member 30.

The first and second guidewire housing members 30, 32 can have lengths L1, L2, respectively measured from a distal open end to a proximal open end thereof. In an arrangement where the proximal ends 42, 54 are aligned axially, the length L1 of the first guidewire housing member 30 is typically longer than the length L2 of the second guidewire housing member 32. The greater length of L1 relative to L2 helps position exposure of the main guidewire extending out of the open distal end 40 of the first guidewire housing member 30 away from the exposed portion of the branch guidewire extending out of the side opening 64. Separation of the main and branch guidewires can help reduce incidence of the main guidewire hindering advancement of the branch guidewire into the branch vessel.

While alternatives are possible, the lengths L1 and L2 can be relatively short, for example in the range of about 10 to about 100 mm (i.e. less than a length from a point exterior of the patient to the vessel bifurcation), or can have lengths L1, L2 that are at least as great as a distance from a point exterior the patient to the vessel bifurcation. In some arrangements, the first and second guidewire housing members 30, 32 can be advanced to the vessel bifurcation using a separate shaft 34. The shaft 34 can be mounted to at least one of the first and second guidewire members 30, 32. FIG. 1 illustrates the shaft 34 having a distal end portion 36 that is connected at least at the proximal ends 42, 54 of the first and second guidewire housing members 30, 32, respectively.

The shaft 34 can be a hollow shaft, a solid shaft or a combination thereof along a length of the shaft 34. The shaft 34 can comprise the same or similar materials that are used for the first and second guidewire housing members 30, 32. In some arrangements, the shaft 34 is connected to the first and second guidewire housing members 30, 32 with, for example, an adhesive, laser welding, or other heat welding.

In still further arrangements, one of the first and second guidewire members 30, 32 has a length that is at least as great as the length extending from a point exterior of the patient to the vessel bifurcation while the other of the guidewire housing members 30, 32 has a shortened length such as in the range of 10 to 100 mm.

The open distal end 40 of the first guidewire housing member is shown in FIG. 1 and the examples shown and described with reference to FIGS. 2-7 below extends distally beyond the side openings 64 a distance, for example, in the range of about 2 to about 20 mm. Alternatives are possible in which the distal ends of the first and second guidewire housing members 30, 32 extend distally an equal distance, or the distal end of the second guidewire housing member 32 extends distally beyond the distal end of the first guidewire housing member 30.

FIGS. 2-8 illustrate some alternative wire assist devices 112, 212, 312, 412. At least some of the example wire assist devices 112, 212, 312, 412 include some features similar to wire assist device 12 and in some cases include alternative configurations for directing the branch guidewire in an angled direction relative to other features of the wire assist device.

Figure 2:
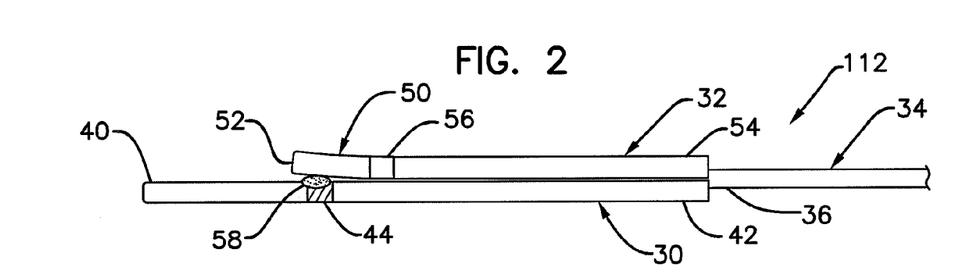
FIG. 2 is a schematic side view of an example wire assisted device in accordance with the principles of the present disclosure, wherein the wire assist device includes an inflatable member in a deflated state.
Figure 3:
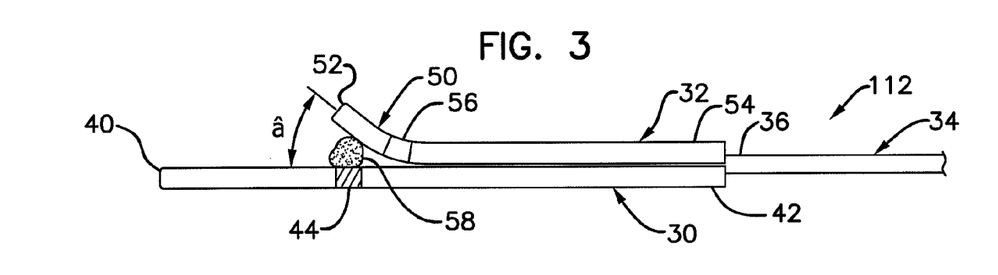
FIG. 3 is a schematic side view of the wire assist device shown in FIG. 1 with the inflatable member in an inflated state.

FIGS. 2 and 3 illustrate a wire assist device 112 that includes a first guidewire housing member having an open distal end 40, an open proximal end 42 and a marker member 44. A second guidewire housing member 32 of the wire assist device 112 includes a distal end portion 50, an open distal end portion 52, an open proximal end 54, a bend region 56, and an inflatable member 58. The inflatable member 58 is positioned in the area of the distal end portion 50 near the open distal end 52. The marker member 44 can illustrate to the operator a location at or near where a branch guidewire can extend distally out of the open distal end 52. Typically, the marker member 44 is arranged in axial alignment with an opening into the branch vessel of a vessel bifurcation, which axial position corresponds with a feature of the second guidewire housing member 32 that directs the second guidewire into the branch vessel.

FIG. 2 illustrates the inflatable member 58 in a deflated state such that the distal end portion 50 is in a first state aligned generally parallel with a longitudinal axis of the wire assist device 112 generally or the first guidewire housing member 30. The arrangement shown in FIG. 2 can be referred to as a first directional arrangement. FIG. 3 illustrates the inflatable member 58 in an inflated state in which the distal end portion 50 bends at the bend region 56 so that the open distal end 52 is facing an angled direction at an angle β relative to the longitudinal axis. The arrangement shown in FIG. 3 can be referred to as a second directional arrangement. The inflatable member 58 can comprise an inflatable balloon member or other structure that can change shapes when inflated and deflated. In one example, the inflatable member 58 can be connected in fluid communication with an inflation lumen provided by, for example, the shaft 34. The inflatable member 58 can be inflated and deflated various amounts to alter the angle β to change the angled direction in which the second guidewire housing member 32 directs a branch guidewire towards an opening of a branch vessel of the vessel bifurcation.

The inflatable member 58 is shown positioned in axial alignment with the marker member 44. In alternative arrangements, the inflatable member 58 can be positioned distal or proximal of the marker 44. Further, the inflatable member 58 can be positioned at various locations relative to the distal open end 52, and the bend region 56. The inflatable member 58 can comprise various shapes and sizes. The generally circular shape of the inflatable member 58 shown in FIG. 3 is merely representative of the inflatable member in an inflated state as compared to the deflated state shown in FIG. 2. Other shapes and sizes for the inflatable member 58 can comprise cylindrical, spherical, and other shapes and sizes.

In some arrangements, the inflatable member 58 is mounted to the first guidewire housing member 30, while in other arrangements an inflatable member is mounted to the second guidewire housing member 32 or both the first and second guidewire housing members 30, 32. In other arrangements, the inflatable member 58 is defined as part of one of the first or second guidewire housing members 30, 32. For example, the inflatable member 58 can be formed in a sidewall of one of the first and second guidewire housing members 30, 32 using a molding process, wherein a portion of the guidewire housing member defines an inflation lumen while another portion of the guidewire housing member defines a guidewire lumen.

Figure 4:
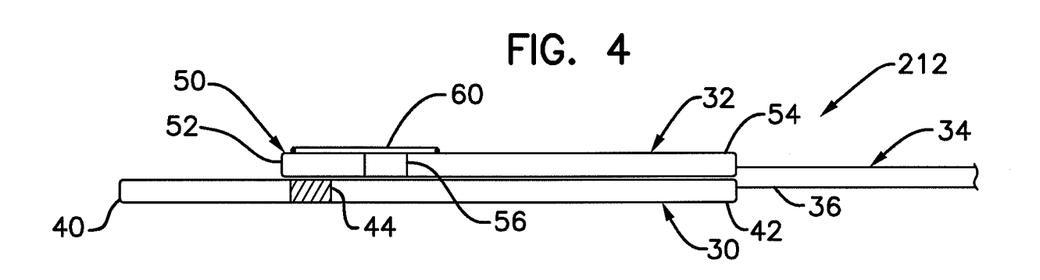
FIG. 4 is a schematic side view of another example wire assist device in accordance with principles of the present disclosure, wherein the wire assist device includes a tether member in a rest state.
Figure 5:
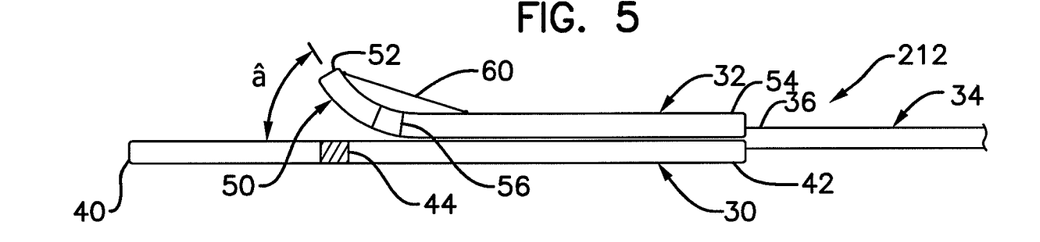
FIG. 5 is a schematic side view of the wire assist device shown in FIG. 3 with the tether member in an activated state.

FIGS. 4 and 5 illustrate another example wire assist device 212 that includes a first guidewire housing member 30, a second guidewire housing member 32, and a shaft 34. The first guidewire housing member 30 includes an open distal end 40, an open proximal end 42, and a marker member 44. The second guidewire housing member 32 includes a distal end portion 50, an open distal end 52, an open proximal end 54, a bend region 56, and a tether member 60. The tether member is connected at a distal end thereof to the second guidewire housing member 32 at a distal side of the bend region 56, while a proximal end of the tether member 60 is positioned at a proximal side of the bend region 56. In one arrangement, a distal end of the tether member 60 is positioned near the open distal end 52, while the proximal end of the tether member 60 is secured to the second guidewire housing member 32 at a location proximal of the distal end of the tether member 60.

The tether member 60 can comprise an activatable material. In one example, the tether member 60 includes an electro active polymer (EAP) material that changes shapes upon activation by an electronic stimulus. In another example, the tether member 60 includes a Nitinol material that changes shape upon a change in temperature of the material. In one example, a tether member 60, when including Nitinol or other shape-changing material, maintains the first unactivated state shown in FIG. 4 when maintained at a first temperature, and changes shape into a second, shorter configuration when activated by application of heat. The increase in temperature of the tether member 60 can be provided by positioning of the wire assist device 212 within the body cavity of the patient, which may occur, for example, after advancing the wire assist device 212 to the vessel bifurcation and permitting a length of time to pass that will change a temperature of the tether member 60.

FIG. 5 illustrates the tether member 60 in an activated state that provides bending of the distal end portion 50 into an angled orientation at an angle β relative to a longitudinal axis of the first guidewire housing member 30.

In other arrangements, more than one tether member 60 can be used to help move the distal end portion 50 into the angled state shown in FIG. 5. When more than one tether member is used, the tether members can be attached to the second guidewire housing member 32 at different axial locations as well as at different radial locations that may be advantageous in altering the angle β at which the distal open end 52 is facing. The tether members 60 can also be used to alter a radial orientation (i.e., side to side) as well as the vertical orientation to define angle β.

The arrangement of the second guidewire housing member 32 shown in FIG. 4 can be defined as a first directional arrangement in which the branch guidewire is arranged substantially parallel with the wire assist device 212 generally or a longitudinal axis of the first guidewire housing member 30. The arrangement of the second guidewire housing member 32 shown in FIG. 5 can be defined as a second directional arrangement in which the branch guidewire can be directed at an angle relative to the wire assist device 212 generally or a longitudinal axis of the first guidewire housing member 30.

Figure 6:
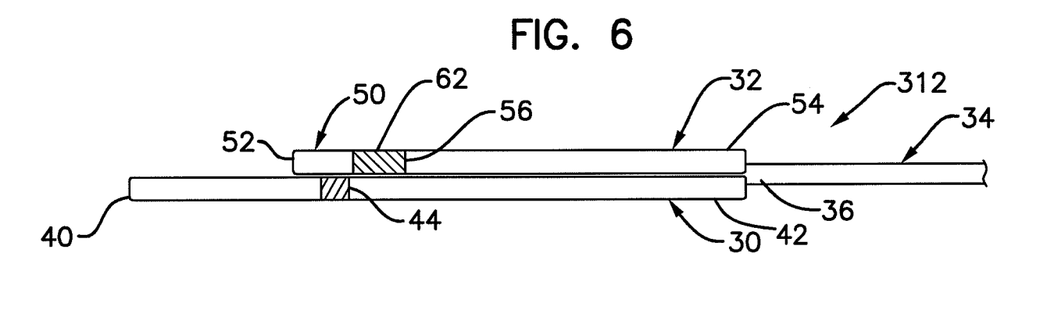
FIG. 6 is a schematic side view of another example wire assist device in accordance with principles of the present disclosure, wherein the wire assist device includes an actuatable bend section in a rest state.
Figure 7:
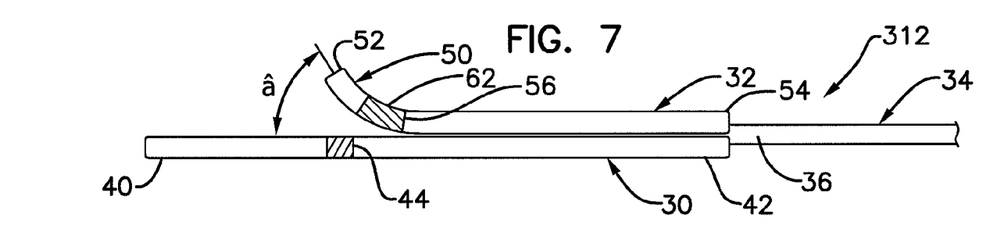
FIG. 7 is a schematic side view of the wire assist device shown in FIG. 5 with the bend section in an activated state.

FIGS. 6 and 7 illustrate another example wire assist device 312 that includes a first guidewire housing member 30, a second guidewire housing member 32, and a shaft 34. The first guidewire housing member 30 includes open distal and proximal ends 40, 42 and a marker member 44. The second guidewire housing member 32 includes a distal end portion, open distal and proximal ends 52, 54, a bend region 56, and a bend actuating material 62. In this arrangement, the bend actuating material 62 is positioned overlapping at least partially with the bend region 56.

The bend actuating material 62 can comprise an electro activated polymer (EAP) that is actuated between a first state having a first shape and size, and a second state having a second shape and size upon receiving an electronic stimulus. In another example, the bend actuating material 62 can comprise a Nitinol or other temperature activated material. The bend actuating material 62, when in a first or rest state as shown in FIG. 6, is aligned generally parallel with the first guidewire housing member 30 in a first directional arrangement. When the bend actuating material 62 is in a second, activated state as shown in FIG. 7, the bend actuating material 62 changes shape to change the direction in which open distal end 52 (i.e., to an angle β). Varying the level of activation of the bend actuating material 62 can change the angle β.

The shape, size, and placement of the bend actuating material 62 can vary in different embodiments. In one example, the bend actuating material 62 is positioned along one side surface of the second guidewire housing member 32 (i.e., along a top surface opposite a position of the first guidewire housing member 30). In another example, the bend actuating material 62 extends around an entire circumference and along at least a portion of the length of the second guidewire housing member 32. The bend actuating material 62 can be imbedded within a side wall of the second guidewire housing member 32. Alternatively, the bend actuating material 62 can be positioned external of the second guidewire housing member 32. When the second guidewire housing member 32 is in the arrangement shown in FIG. 7 with the bend actuating material 62 at least partially activated, the second guidewire housing member 32 is in a second directional arrangement in which the branch guidewire can be directed at an angle relative to the wire assist device 312 generally or a longitudinal axis of the first guidewire housing member 30.

Figure 8:
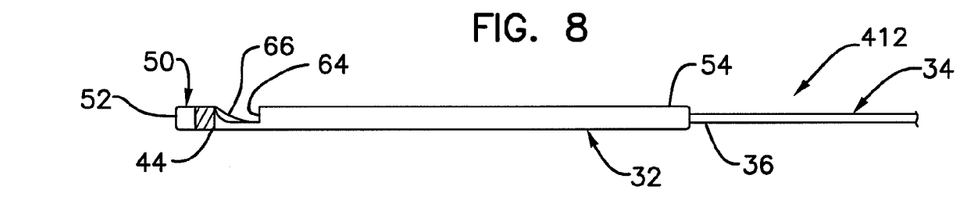
FIG. 8 is a schematic side view of another example wire assist device in accordance with principles of the present disclosure, wherein the wire assist device includes a single guidewire housing member having a side opening.

FIG. 8 illustrates a still further wire assist device 412 that includes a single guidewire housing member 32. The guidewire housing member 32 includes a distal end portion 50, open distal and proximal ends 52, 54, a side opening 64, a flap 66, and a marker member 44. The guidewire housing member 32 shown in FIG. 8 is mounted to a shaft 34, although in other arrangements the shaft 34 can be replaced by an elongate version of the guidewire housing member 32.

In other arrangements, three or more guidewire housing members can be used. In one example, a third guidewire housing member is included adjacent the first and second guidewire housing members 30, 32 for advancement over a place holding guidewire (not shown). A place holding guidewire can sometimes be advanced to the vessel bifurcation within the main vessel distally beyond the branch guidewire using a three housing member arrangement, followed by retraction of at least a main guidewire. In other instances, a place holding guidewire is positioned in the main vessel prior to advancing the main and branch guidewires to the vessel bifurcation, wherein the three guidewire housing member is used to swap the place holding guidewire with a main guidewire and advance the branch guidewire into the branch vessel. The three guidewire housing member can help resolve relative twist between any three guidewires that may be positioned in the vessel.

The side opening 64 and flap 66 included in wire assist device 412 can have the same or similar features and functionality as described above with reference to FIG. 1. The marker member 44 can be positioned axially adjacent to or at least partially overlapping the axial position of the side opening 64 to provide visualization of the axial position of the side opening 64 relative to the vessel bifurcation. The wire assist device 412 can be particularly useful in a method of treating a vessel bifurcation when a main guidewire is not pre-positioned within the main vessel of the vessel bifurcation. However, the wire assist device 412 can be used in a treatment method in which a main guidewire is pre-positioned in the main vessel and the wire assist device 412 is advanced over the branch guidewire alone. In such an arrangement, the wire assist device 412 may not address reduction of relative twists between main and branch guidewires, but can still be useful in advancing the branch guidewire from the main vessel into the branch vessel at the vessel bifurcation.

The bend region 56 illustrated in FIGS. 2-7 can include a reduced thickness of the second guidewire housing member 32 along at least a portion of the length and around at least a portion of the circumference of the second guidewire housing member 32. Reducing the thickness of the second guidewire housing member 32 in this way can promote intended bending of portions of the distal end portion 50. In some instances, the bend region can improve the range of the angle β relative to the length of the distal end portion. For example, providing a bend region can increase the angle β to greater than 90°.

Example Treatment Methods of FIGS. 9-13

Referring now to FIGS. 9-13, an example method of treating a vessel bifurcation 18 is shown and described. A vessel bifurcation 18 includes a main vessel 20 and a branch vessel 22. In a first example method, a main guidewire 14 is advanced until a distal end thereof is positioned distal of an opening or ostium 24 into the branch vessel 22. A branch guidewire 16 is advanced distally to a point where a distal end thereof is positioned proximal of the ostium 24.

Figure 10:
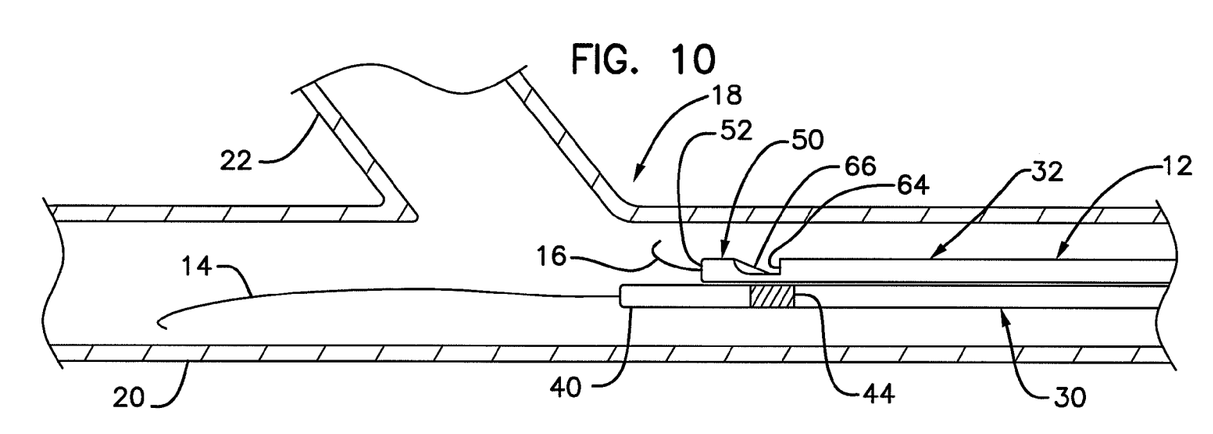
FIG. 10 is a schematic side view of the vessel bifurcation shown in FIG. 9 with a wire assist device advanced over the main and branch guidewires.
Figure 11:
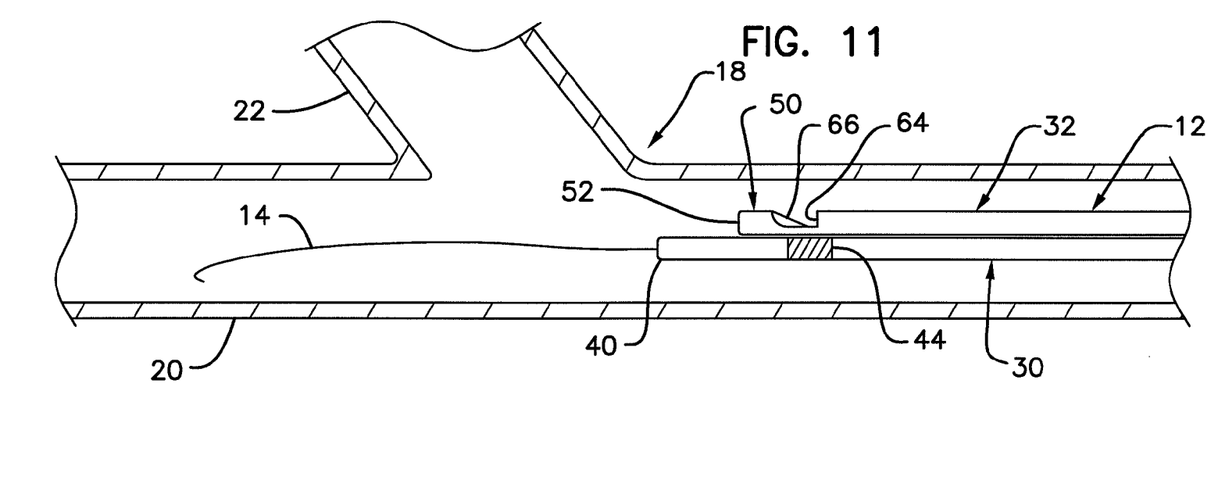
FIG. 11 is a schematic side view of the wire assist device shown in FIG. 10 with the branch guidewire retracted proximally within a second guidewire housing member of the wire assist device.

FIG. 10 illustrates the wire assist device 12 advanced distally to a point adjacent to the vessel bifurcation 18 with the distal end of the branch guidewire 16 protruding distally out of the open distal end 52. FIG. 11 illustrates the branch guidewire 16 being retracted proximally relative to the wire assist device 12 so that a distal end thereof is positioned proximal of the side opening 64. As described below, the flap 66 can be moveable within the cut 64 to permit passage of the branch guidewire 16 as shown in FIG. 10, while in FIG. 11 the flap 66 lays down within the guidewire lumen defined within the second guidewire housing 32 when the branch guidewire 16 is retracted proximally of the side opening 64.

Figure 12:
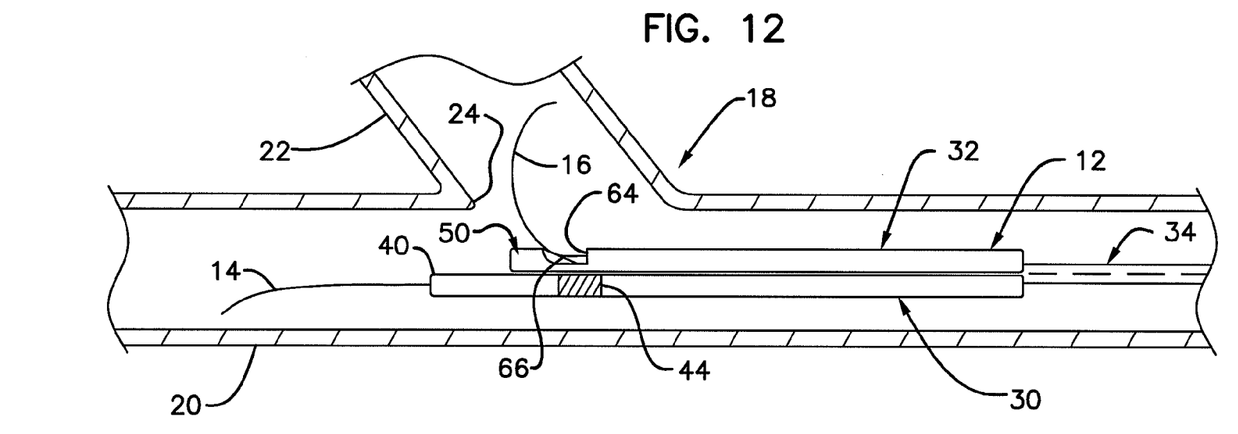
FIG. 12 is a schematic side view of the wire assist device shown in FIG. 10 with the branch guidewire extending through a side opening of the second guidewire housing member and into the branch vessel of the vessel bifurcation.

FIG. 12 illustrates the wire assist device 12 positioned adjacent to the ostium 24 with the side opening 64 aligned axially and radially relative to the ostium 24. The marker member 44 can assist in helping the operator make such an axial and radial alignment. The branch guidewire 16 is shown advanced distally into contact with the ramp surface defined by the flap 66, which directs the branch guidewire 16 in an angled direction relative to a longitudinal axis of the wire assist device 12. The branch guidewire 16 is advanced distally until a distal end thereof is positioned within the branch vessel 22 while the main guidewire 14 remains within the main vessel 20.

Figure 13:
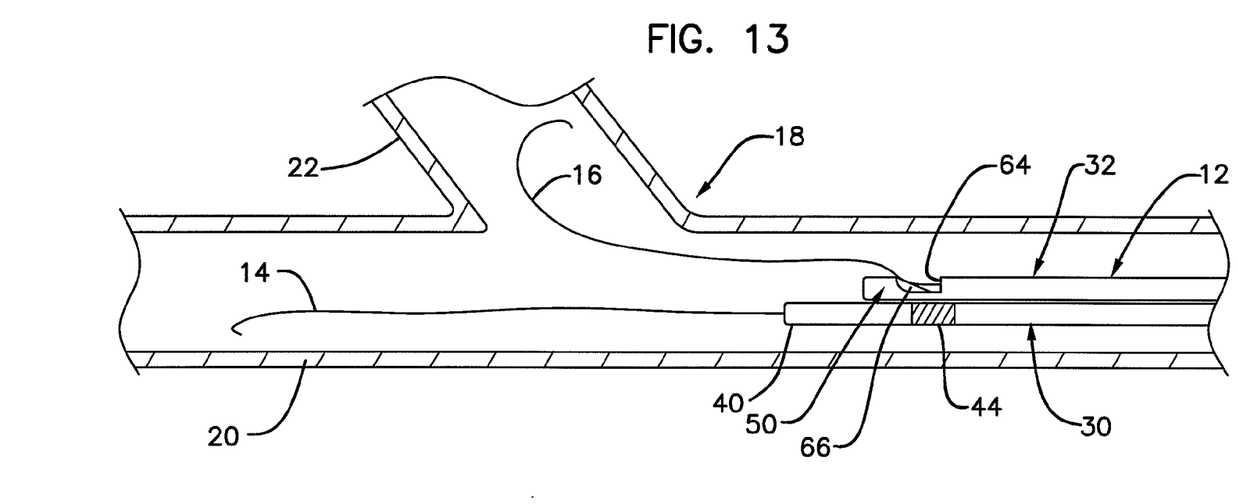
FIG. 13 is a schematic side view of the wire assist device shown in FIG. 12 with the wire assist device retracted proximally leaving the main and branch guidewires positioned within the main and branch vessels, respectively, of the vessel bifurcation.

FIG. 13 illustrates the wire assist device 12 retracted proximally while the branch guidewire 16 remains positioned within the branch vessel 22 and the main guidewire 14 remains within the main vessel 20. With the guidewires properly positioned within the vessels 20, 22, a catheter assembly can be advanced over the guidewires 14, 16 for treatment of the vessel bifurcation 18.

Figure 9:
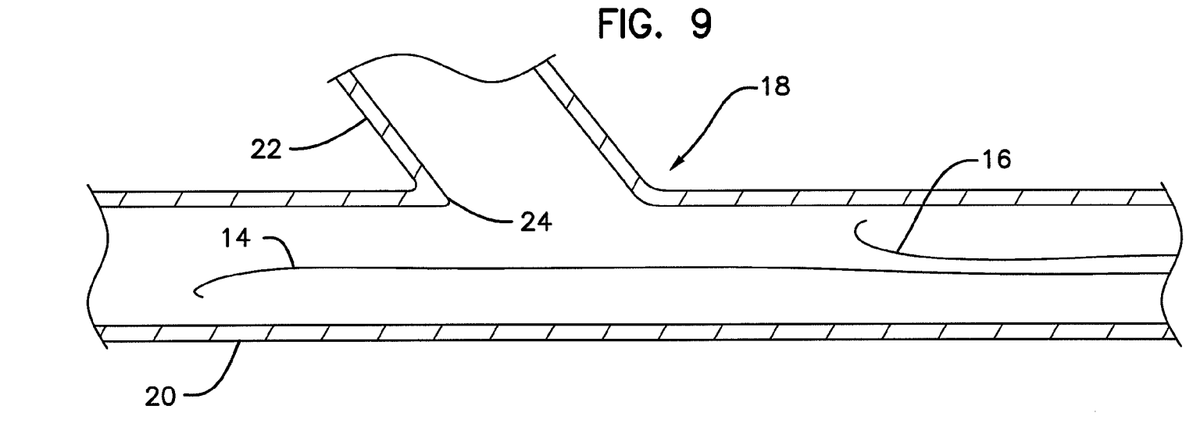
FIG. 9 is a schematic side view of a vessel bifurcation, wherein a main guidewire is positioned in a main vessel and a branch guidewire is positioned proximal of the vessel bifurcation.

There can be several variations of the method described above with reference to FIGS. 9-13. For example, in one alternative method the main guidewire 14 is pre-positioned within the main vessel 20 as shown in FIG. 9, but the branch guidewire 16 is pre-positioned within the second guidewire housing 32 with a distal end thereof positioned proximal of the side opening 64. The branch guidewire is advanced concurrently with advancement of the wire assist device 12 to the vessel bifurcation 18. The wire assist device 12 is then adjusted axially and radially until the side opening 64 is aligned with the ostium 24, wherein the branch guidewire 16 is then advanced distally into engagement with the flap 66 to be directed into the branch vessel 22.

In another example method, the branch guidewire 16 is pre-positioned with a distal end thereof positioned proximal of the vessel bifurcation 18 as shown in FIG. 9, and the main guidewire 14 is not yet advanced to the vessel bifurcation. The main guidewire 14 is pre-positioned within the first guidewire housing member 30 of the wire assist device 12 and advanced along with the wire assist device 12 to the vessel bifurcation. Once the wire assist device 12 is positioned at the vessel bifurcation, the main guidewire 14 is advanced distally to a location wherein a distal end thereof is positioned distal of the ostium 24. The branch guidewire 16 is retracted within the second guidewire housing member 32 until a distal end thereof is positioned proximal of the side opening 64. Then the steps described above with reference to FIGS. 12 and 13 are performed to position the branch guidewire 16 within the branch vessel 22.

Modifications in the various example methods of positioning the branch guidewire within the branch vessel 22 of the vessel bifurcation 18 can be made in order to better utilize the wire assist devices 112, 212, 312, 412 described above. For example, instead of advancing the branch guidewire 16 into engagement with the ramp surface defined by flap 66 after orienting a side opening 64 with the ostium 24, the method may include first moving the distal end portion 50 into an activated or bent state as shown in FIGS. 3, 5 and 7, followed by advancing the branch guidewire 16 into the branch vessel 22.

The wire assist device as disclosed with reference to FIGS. 1-7 can be used primarily for the purpose of reducing relative twists between a main and branch guidewires even if the wire assist device is not used to direct a branch guidewire into a branch vessel. When the main and branch guidewires 14, 16 are positioned at or adjacent to the vessel bifurcation 18, advancing a wire assist device with first and second guidewire housing members over the main and branch guidewires 14, 16 can help undo some of the relative twists between the guidewires. Such untwisting of the guidewires 14, 16 may be sufficient alone to provide the operator with the needed adjustability to direct the branch guidewire 16 into the branch vessel 22 without the use of features on a wire assist device that help direct the branch guidewire at an angle relative to the longitudinal axis of the wire assist device. For example, a wire assist device that merely includes first and second guidewire housing members without any features to help direct a branch guidewire at an angle (i.e. a wire assist device having a second guidewire housing member that includes a single directional arrangement instead of the first and second directional arrangements described above) can be advanced over the main and branch guidewires to eliminate or otherwise undo some of the relative twists therebetween. After such reduction in relative twists, the wire assist device can be retracted proximally, re-advanced as needed to further reduce relative twists, still further retracted proximally, followed by the operator independently advancing the branch guidewire into the branch vessel of the vessel bifurcation.

Materials and Other Considerations

The materials used in the catheter shafts and guidewire housing members disclosed herein can be made of any suitable material including, for example, thermoplastic polymers, polyethylene (high density, low density, intermediate density, linear low density), various co-polymers and blends of polyethylene, ionomers, polyesters, polycarbonates, polyamides, poly-vinyl chloride, acrylonitrile-butadiene-styrene copolymers, polyether-polyester copolymers, and polyetherpolyamide copolymers. One suitable material is Surlyn®, a copolymer polyolefin material (DuPont de Nemours, Wilmington, Del.). Still further suitable materials include thermoplastic polymers and thermoset polymeric materials, poly(ethylene terephthalate) (commonly referred to as PET), thermoplastic polyamide, polyphenylene sulfides, polypropylene. Some other example materials include polyurethanes and block copolymers, such as polyamide-polyether block copolymers or amide-tetramethylene glycol copolymers. Additional examples include the PEBAX® (a polyamide/polyether/polyester block copolymer) family of polymers, e.g., PEBAX® 70D, 72D, 2533, 5533, 6333, 7033, or 7233 (available from Elf AtoChem, Philadelphia, Pa.). Other examples include nylons, such as aliphatic nylons, for example, Vestamid L21011F, Nylon 11 (Elf Atochem), Nylon 6 (Allied Signal), Nylon 6/10 (BASF), Nylon 6/12 (Ashley Polymers), or Nylon 12. Additional examples of nylons include aromatic nylons, such as Grivory (EMS) and Nylon MXD-6. Other nylons and/or combinations of nylons can also be used. Still further examples include polybutylene terephthalate (PBT), such as CELANEX® (available from Ticona, Summit, N.J.), polyester/ether block copolymers such as ARNITEL® (available from DSM, Erionspilla, Ind.), e.g., ARNITEL® EM740, aromatic amides such as Trogamid (PA6-3-T, Degussa), and thermoplastic elastomers such as HYTREL® (Dupont de Nemours, Wilmington, Del.). In some embodiments, the PEBAX®, HYTREL®, and ARNITEL® materials have a Shore D hardness of about 45D to about 82D. The balloon materials can be used pure or as blends. For example, a blend may include a PBT and one or more PBT thermoplastic elastomers, such as RITEFLEX® (available from Ticona), ARNITEL®, or HYTREL®, or polyethylene terephthalate (PET) and a thermoplastic elastomer, such as a PBT thermoplastic elastomer. Additional examples of balloon material can be found in U.S. Pat. No. 6,146,356. It should be understood that the specific materials disclosed below for the individual embodiments does not limit the embodiment to those materials.

In the examples described above, some of the features can include a lubricious coating on an exterior surface thereof. The coating can promote insertion of the device at the vessel bifurcation. The coating can also improve removal of the device from the vessel bifurcation. Some example coating for use with the example devices include hydrophilic polymers such as polyarylene oxides, polyvinylpyrolidones, polyvinylalcohols, hydroxyl alkyl cellulosics, algins, saccharides, caprolactones, and the like, and mixtures and combinations thereof. Hydrophilic polymers can be blended among themselves or with formulated amounts of water insoluble compounds (including some polymers) to yield coating with suitable lubricity, bonding and solubility. In some examples, portions of the devices described herein can be coated with a hydrophilic polymer or a fluoropolymer such as polytetrafluoroethylene (PTFE), better known as TEFLON®.

Conclusion

One aspect of the present disclosure relates to a bifurcated vessel wiring assist device. The wiring assist device includes first and second guidewire housing members. The first guidewire housing member defines a first guidewire lumen that is sized to advance over a first guidewire. The first guidewire housing member can include longitudinal axis defined along a length of the first guidewire housing member. The second guidewire housing member defines a second guidewire lumen that is sized to advance over a second guidewire. The second guidewire housing member is axially fixed relative to the first guidewire housing member and includes a distal end portion. The distal end portion includes a first directional arrangement and a second directional arrangement, wherein the first directional arrangement provides a parallel arrangement of the second guidewire relative to the longitudinal axis, and the second directional arrangement provides an angled arrangement of the second guidewire relative to the longitudinal axis.

Another aspect of the present disclosure relates to a bifurcated vessel wiring assist assembly that includes a main vessel and a branch vessel. The wiring assist assembly includes a main guidewire, a branch guidewire, a first guidewire housing member, and a second guidewire housing member. The main guidewire is adapted for positioning in the main vessel. The branch guidewire is adapted for positioning in the branch vessel. The first guidewire housing member defines a first guidewire lumen sized to advance over the first guidewire and can include a longitudinal axis defined along a length of the first guidewire housing member. The second guidewire housing member defines a second guidewire lumen sized to advance over the second guidewire. The second guidewire housing member has a first directional arrangement and a second directional arrangement, wherein the first directional arrangement provides a parallel arrangement of the second guidewire relative to the longitudinal axis, and the second directional arrangement provides an angled arrangement of the second guidewire relative to the longitudinal axis.

A still further aspect of the present disclosure relates to a method of advancing a branch guidewire into a branch vessel of a vessel bifurcation using a wiring assist device. The wiring assist device includes a first guidewire housing member and a second guidewire housing member. The first guidewire housing member defines a first guidewire lumen. The second guidewire housing member defines a second guidewire lumen, a first directional arrangement and a second directional arrangement, wherein the first directional arrangement provides a parallel arrangement of the second guidewire relative to the longitudinal axis, and the second directional arrangement provides an angled arrangement of the second guidewire relative to the longitudinal axis. The method can include steps of positioning a main guidewire in a main vessel of the vessel bifurcation, and advancing the first guidewire housing member over the main guidewire to the vessel bifurcation with the second guidewire housing member in the first directional arrangement, wherein the first directional arrangement provides a parallel arrangement of the branch guidewire relative to the main guidewire. The method can also include directing the branch guidewire into the branch vessel with the second guidewire housing member in the second directional arrangement, wherein the second directional arrangement provides an angled orientation of the branch guidewire relative to the main guidewire.

The above specification, examples and data provide a complete description of the manufacture and use of the composition of the invention. Since many embodiments of the invention can be made without departing from the spirit and scope of the invention, the invention resides in the claims hereinafter appended.

We claim:

1. A method of advancing a branch guidewire into a branch vessel of a vessel bifurcation using a wiring assist device, the wiring assist device including a first guidewire housing member and a second guidewire housing member, the first guidewire housing member having a longitudinal axis and defining a first guidewire lumen, the second guidewire housing member defining a second guidewire lumen and having a distal end portion including an open distal end through which the second guidewire may advance distally, the distal end portion including an activatable material activatable to move the second guidewire housing member from a first directional arrangement to a second directional arrangement, the first directional arrangement providing a parallel arrangement of the second guidewire relative to the longitudinal axis, and the second directional arrangement providing an angled arrangement of the second guidewire relative to the longitudinal axis, the method comprising:

(a) positioning a main guidewire in a main vessel of the vessel bifurcation;
    (b) positioning a branch guidewire adjacent the vessel bifurcation;
    (c) advancing the first guidewire housing member over the main guidewire and the second guidewire housing member over the branch guidewire to the vessel bifurcation with the second guidewire housing member in the first directional arrangement, wherein the first directional arrangement provides a parallel arrangement of the branch guidewire relative to the main guidewire;
    (d) activating the activatable material, thereby moving the second guidewire housing member from the first directional arrangement to the second directional arrangement;
    (e) directing the branch guidewire into the branch vessel with the second guidewire housing member in the second directional arrangement, wherein the second directional arrangement provides an angled orientation of the branch guidewire relative to the main guidewire;
    (f) withdrawing the wiring assist device from the main vessel while maintaining the main guidewire in the main vessel and maintaining the branch guidewire in the branch vessel; and
    (g) advancing a medical device over the main and branch guidewires.

2. The method of claim 1, wherein the activatable material includes a Nitinol material or an electro active polymer (EAP) material, and the activating step includes applying heat or electricity to activate the Nitinol or EAP, respectively.

3. The method of claim 1, wherein moving the second guidewire housing member includes inflating a balloon member, at least a portion of the balloon member being positioned between the first guidewire housing member and the second guidewire housing member.

4. The method of claim 1, wherein the wire assist device includes a marker member arranged in axial alignment with a portion of the second guidewire housing member, the method further comprising aligning the marker member with an opening into the branch vessel of the vessel bifurcation.

* * * * *